US009168167B2

(12) United States Patent
Brown (10) Patent No.: US 9,168,167 B2
(45) Date of Patent: Oct. 27, 2015

(54) POSTURE IMPROVEMENT DEVICE AND METHOD OF USE

(75) Inventor: Timothy W. Brown, Laguna Beach, CA (US)

(73) Assignee: AlignMed, Inc., Santa Ana, CA (US)

( * ) Notice: Subject to any disclaimer, the term of this patent is extended or adjusted under 35 U.S.C. 154(b) by 521 days.

(21) Appl. No.: 12/974,867

(22) Filed: Dec. 21, 2010

(65) Prior Publication Data

US 2011/0213283 A1 Sep. 1, 2011

Related U.S. Application Data

(63) Continuation of application No. 10/795,656, filed on Mar. 8, 2004, now Pat. No. 7,871,388.

(51) Int. Cl.
*A61F 5/00* (2006.01)
*A61F 5/03* (2006.01)
*A61F 5/02* (2006.01)
*A61F 5/34* (2006.01)
*A61F 5/37* (2006.01)
*A61N 1/04* (2006.01)
*A41D 13/00* (2006.01)
*A61N 1/36* (2006.01)

(52) U.S. Cl.
CPC . *A61F 5/03* (2013.01); *A61F 5/026* (2013.01); *A61F 5/34* (2013.01); *A61F 5/3746* (2013.01); *A61N 1/0484* (2013.01); *A41D 13/0015* (2013.01); *A61N 1/36003* (2013.01)

(58) Field of Classification Search
CPC ........... A61F 5/03; A61F 5/026; A61F 5/028; A61F 5/34; A61N 1/04084; A61N 1/36003; A41D 13/0015; A41D 13/0512; A41D 13/0518; A41B 1/08

USPC .............. 602/4, 5, 19, 20; 2/44, 45, 102, 104; 128/873, 874

See application file for complete search history.

(56) References Cited

U.S. PATENT DOCUMENTS

| 2,418,009 | A | * | 3/1947 | Berman ............................... 2/44 |
| 2,586,658 | A | * | 2/1952 | Hormann ......................... 450/96 |
| 3,116,735 | A | * | 1/1964 | Geimer ............................. 450/2 |
| 3,663,797 | A | * | 5/1972 | Marsh ............................ 219/211 |
| 4,785,803 | A | * | 11/1988 | Benckhuijsen .................. 602/20 |
| 5,306,229 | A | * | 4/1994 | Brandt et al. ................... 602/26 |
| 5,344,384 | A | * | 9/1994 | Ostrow et al. ................... 600/13 |
| 5,555,566 | A | | 9/1996 | Kuhn |
| 5,857,990 | A | | 1/1999 | Maas |
| 5,937,442 | A | | 8/1999 | Yamaguchi et al. |
| 6,176,816 | B1 | | 1/2001 | Dicker et al. |
| 6,306,111 | B1 | | 10/2001 | Dean |

(Continued)

*Primary Examiner* — Kim M Lewis
(74) *Attorney, Agent, or Firm* — Schiff Hardin LLP (57) ABSTRACT

Provided is a device for improving the posture of a patient comprising a garment and a pair of tension straps. The garment is configured to tightly envelope the patient's torso and the patient's upper arms. The garment has an inner surface, a front side and a back side. The front side includes a chest portion. The back side includes a back portion. The garment defines opposing shoulder portions and a waist portion. The tension straps are releaseably securable to the back portion in diagonal relation to one another. Each one of the tension straps has opposed free ends that extend upwardly from the back portion to the chest portion and downwardly to the waist portion. The device includes pads releaseably mounted on the inner surface of the garment generally opposite the free ends and are configured to restrict movement of the free ends relative to the patient's skin.

15 Claims, 6 Drawing Sheets

(56) References Cited

U.S. PATENT DOCUMENTS

| | | | |
|---|---|---|---|
| 6,440,094 B1 * | 8/2002 | Maas | 602/5 |
| 6,464,656 B1 | 10/2002 | Salvucci et al. | |
| 6,936,021 B1 | 8/2005 | Smith | |
| 6,945,945 B2 | 9/2005 | Givler et al. | |
| 7,037,284 B2 | 5/2006 | Lee | |
| 8,007,457 B2 * | 8/2011 | Taylor | 602/75 |
| 2002/0143373 A1 * | 10/2002 | Courtnage et al. | 607/91 |
| 2008/0208089 A1 | 8/2008 | Newkirk et al. | |

* cited by examiner

POSTURE IMPROVEMENT DEVICE AND METHOD OF USE

CROSS-REFERENCE TO RELATED APPLICATIONS

This U.S. Utility Patent Application is a continuation application under 35 U.S.C. 120 of commonly assigned U.S. patent application Ser. No. 10/795,656 entitled Posture Improvement Device and Method of Use, filed Mar. 8, 2004, the contents of which are hereby incorporated by reference in their entirety.

BACKGROUND OF INVENTION

The present invention relates generally to body mechanics and, more particularly, to a posture improvement device configured to be worn on a user's torso and which is specifically adapted to improve the user's body alignment or posture through the use of neuromuscular stimulation.

The importance of good posture is well known among health professionals. Posture generally refers to the alignment of the body, and more specifically, to the relative static and dynamic positioning of the body and its limbs. Ideally, in a body exhibiting good posture, the spine has no lateral curvature and the legs have little angulation in the knees and ankles. In addition, when viewed from the side, the spine forms a slight S-shape with the two curves of the S-shape being evenly disposed on opposite sides of an imaginary line extending downwardly from the head through the body's center. Such an alignment provides an even distribution of body weight over the spine and lower body joints resulting in a relatively uniform distribution of pressure on the intervertrebral discs of the spine.

The effects of poor posture are well documented and include limited range of motion wherein muscles, such as the pectoral muscles in the chest, may be permanently shorted due to a hunched-over upper body position. Other effects of poor posture include discomfort in the form of headaches at the base of the skull and pain in the shoulders, aims, and hands. Additionally, poor posture may lead to pain in the jaw due to a forward-head position as well as decreased lung capacity due to decreased volume of the chest cavity and lungs. One of the most common consequences of poor posture is the onset of lower back pain which may increase with advancing age. Finally, a hunched-over upper body position of poor posture can add years to one's appearance.

However, by assuming good posture, gravitational forces may be more evenly distributed throughout the bones, ligaments and muscles of the body. Maintaining good posture is equally important during passive (static) activities such as sitting and standing as well as during dynamic activities such as walking, running, lifting, etc. Theoretically, the slight S-shape of the spine that is characteristic of good posture should preferably be maintained during both static and dynamic activities. Unfortunately, our increasingly sedentary lifestyle wherein many hours are spent sitting in front of a computer, driving an automobile, or watching television has an adverse effect of posture. Such static activities may result in forward protrusion of the head and neck rounding of the thoracic and lumbar spine and stretching of the spinal ligaments. Such stretching gradually causes pain in the neck and upper back and results in fatigued of the body's muscles and ligaments. Poor posture during dynamic activities such as such as running and lifting results in inefficient body movements with increased stress on muscles and ligaments.

Maintaining an awareness of proper posture during static and dynamic activities may sometimes prevent overstressing muscles and ligaments. In addition, maintaining an awareness of proper posture may train certain muscles through muscle memory such that proper posture eventually becomes a habit. However, it is sometimes difficult to maintain an awareness of proper posture during mentally challenging activities such as working at a computer or during physically challenging activities such as participating in aggressive sports. Physical therapists may utilize postural therapy to improve the posture of a patient. Such postural therapy may include techniques such as shoulder taping and breathing exercises. Conventional chiropractic techniques may utilize body manipulation and treatment to help keep the patient's spine in alignment. However, the patient must take the time and energy to visit the offices of a physical therapist or a chiropractor in order to receive the needed postural therapy and/or chiropractic manipulation. Furthermore, alternative treatment, such as cutaneous nerve stimulation, is often overlooked as a method to improve the patient's posture.

As can be seen, there exists a need in the art for a device that is specifically adapted to continuously train and develop certain body muscles such that the patient's posture may be improved. In addition, there exists a need in the art for a device that allows for developing such muscle training during static activities such as standing and sitting. In addition, there exists a need in the art for a device that discretely allows for developing such muscle training during dynamic activities such as walking, running and during other daily activities. Furthermore, there exists a need in the art for a device for improving the patient's posture that may be progressively adjusted in accordance with changes or improvements in the patient's posture over time. Finally, there exists a need in the art for a device for improving the patient's posture that may be adjusted according to varying physiological parameters between patients including differences in patient age, body size, muscular development and underlying pathophysiologic status.

BRIEF SUMMARY OF THE INVENTION

Provided in the invention is a posture improvement device that is specifically adapted to provide neuromuscular stimulation or proprioceptive therapy using a combination of pressure, torque and angle simultaneously applied to the patient in order to train body muscles for proper posture through muscle memory. The device comprises a garment configured to be worn by a patient or user and which is configured to envelop at least a portion of the patient's torso and at least a portion of the patient's upper arms, which is configured like a short-sleeved undershirt or T-shirt. The device also includes a pair of tension straps releasably secured to a back side, to a waist portion, and to shoulder portions of the garment. The tension straps are diagonally disposed relative to one another on the back side of the garment. The tension straps are configured to be stretchable in a manner such that the patient's shoulders may be pulled or biased downwardly while the patient's chest is simultaneously pulled or biased upwardly.

Pressure is applied to the patient's (user's) skin in order to proprioceptively stimulate cutaneous nerve receptors of the skin by configuring the garment as a relatively tight, form-fitting shirt. The garment is configured to envelope at least a portion of the patient's torso and at least a portion of the patient's upper arms. The garment has an inner and an outer surface, a front side, a back side, opposing lateral sides, and a pair of partial sleeves. The front side includes a chest portion and a stomach portion, while the back side includes a back portion. The garment also defines opposing shoulder portions and a waist portion extending about a lower end of the garment. The short-sleeved configuration of the garment allows for effective training of the patient's pectoralis major muscles located in the patient's chest. In addition, the short-sleeved configuration of the garment enhances the patient's range of motion, particularly at the shoulder joints, in addition to providing conditioning of the patient's rotator cuffs.

The garment may be fabricated from stretchable yet taut material in order to provide the desirable form-fitting feature such that pressure may be readily applied to the surface of the skin for neuromuscular stimulation. In this regard, the garment is preferably fabricated of eslastomeric material that is also preferably breathable and/or which has moisture wicking capabilities such as may be provided by a material comprised of a combination of Lycra and Spandex.

The tension straps are releaseably securable to the back portion in diagonal relation to one another such that anatomical differences in patients may be accommodated as well as allowing the device to pull each one of the patient's shoulders backwardly in order to correct for forward slouching of the patient's shoulders as is sometimes characteristic of poor posture. Each one of the tension straps has opposed free ends that are configured to be releaseably securable to the garment at the chest and stomach portions. An upper one of the free ends of each one of the tension straps is releaseably secured to the chest portion on the outer surface of the front side of the garment.

Furthermore, the tension straps are releaseably secured to the back portion on the back side of the garment at an approximate center of the back portion. Finally, a lower end of each one of the tension straps is releaseably secured to the waist portion on the front side of the garment. In this manner, each one of the tension straps extends upwardly from the chest portion adjacent one of the lateral sides, arches over one of the shoulder portions, passes diagonally across the back portion, partially wraps about the patient's torso on the opposing one of the lateral sides, and terminates at the waist portion on the front side.

The diagonal orientation of the tension straps results in the application of torque to the patient's torso using a dual-anchor configuration of the straps. A first anchor is provided by the tension straps extending from the chest portion, over the shoulder portion to correct for over-toned or shortened chest muscles due to a forward slouching position. A second anchor is provided by extension of the tension straps from the back portion on the back side and partially wrapping about the patient's torso to terminate at the waist portion on the front side of the garment. An elongate, extendable waist band may be secured to the waist portion on the back side of the garment with opposing free ends extending laterally outwardly therefrom and wrapping partially around the patient's torso for releaseable securement to the waist portion on the front side. The waist band and tension bands may be fabricated of elastomeric material such as Neoprene although a variety of other materials may be used.

Each one of the tension straps may include a hook and loop panel, more commonly referred to by the trademark VELCRO®, mounted adjacent to a strap midpoint to allow for anchoring of the tension straps on a hook and loop panel of the back portion. The generally large size of the hook and loop panel of the back portion allows for flexibility in positioning of the tension straps as well as allowing for progressive adjustment of tension in the tension straps during the course of wearing the device. Each one of the free ends of the tension straps may include a hook and loop panel for attachment thereto to the chest portion and to the waist portion. The free ends of the tension straps and of the waistband may each be releaseably securable, via hook and loop panels mounted thereon to allow for adjustment of tension in the tension bands and in the waist band. Although hook and loop panels are described as providing the means for securing the tension straps and waist band to the garment, it should be noted that any equivalent attachment means, known to those of ordinary skill in the art, may be utilized, such as buttons, snaps, hooks, other mechanical fasteners, or any suitable means.

A pair of viscoelastic pads may be releaseably mounted on the inner surface at the chest portion and are preferably positioned adjacent to the patient's pectoralis major muscles located on the patient's chest in order to prevent slippage and to restrict movement of the free ends of the chest portion. In addition, neuromuscular stimulation may be provided by the viscoelastic pads to the patient's skin to enhance posture correction. A pair of L-shaped viscoelastic pads may be releaseably mounted on the back portion of the garment below each one of the shoulder portions so as to be partially engagable with the patient's scapula which is generally located on the patient's back adjacent the patient's rib cage. Engagement of the L-shaped viscoelastic pads with the patient's skin may limit dynamic movement of the tension straps during body movements of the patient.

Furthermore, the L-shaped viscoelastic pads may help stabilize and enhance the development of proper posture. The viscoelastic pads are preferably fabricated from flexible, rubber like material such as silicone rubber although any resilient material may be used to provide a soft and semi-tacky surface to comfortably bear against the patient's skin and which will prevent relative slippage or movement of the tension straps. Each one of the viscoelastic pads may include a heating element to provide localized heat therapy to the patient's torso through elevation of the temperature of the viscoelastic pads. Furthermore, each one of the viscoelastic pads may include an electrostimulation element configured to provide and enhance neuromuscular stimulation to the patient's torso in order to enhance the development of proper posture when the device is worn.

BRIEF DESCRIPTION OF THE DRAWINGS

These as well as other features to the present invention will become more apparent upon reference to the drawings wherein.

DETAILED DESCRIPTION OF THE INVENTION

Referring now to the drawings wherein the showing are for purposes of illustrating the present invention and not for purposes of limiting the same, FIGS. 1-8 are views of a posture improvement device 10 in accordance with a preferred embodiment wherein the device 10 comprises a garment 16 configured to be worn by a patient and which is configured to envelope at least a portion of the patient's torso 12 and at least a portion of the patient's upper arms 14. In this regard, the garment 16 forms a shape commonly referred to as a short-sleeved undershirt or a T-shirt. The device 10 also includes a pair of elongate, extendable tension straps 42 releaseably secured to a back side 30, to a waist portion 38 and to shoulder portions 34 of the garment 16. The tension straps 42 are diagonally disposed relative to one another are releaseably secured to the back side 30 of the garment 16.

Figure 9:
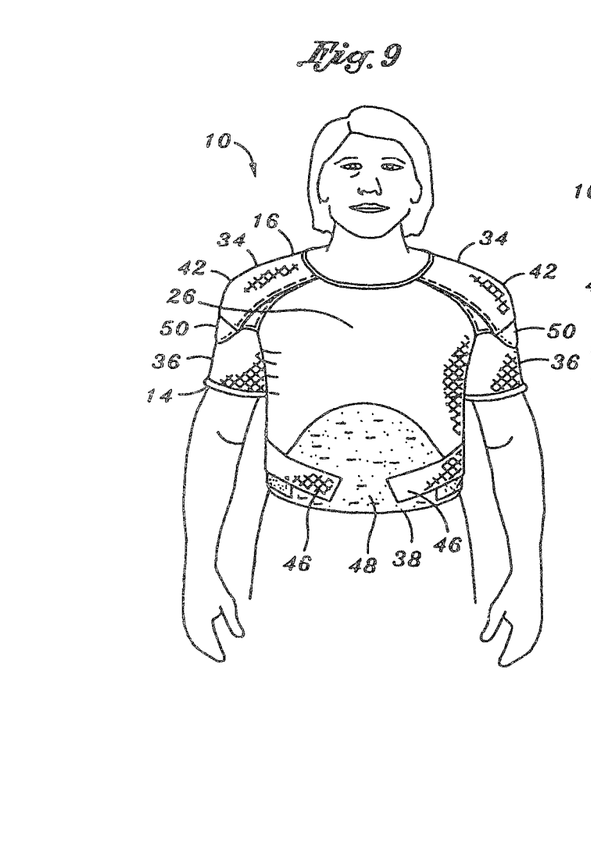
FIG. 9 is a front view of the posture improvement device in an alternative embodiment as worn by the patient.
Figure 11:
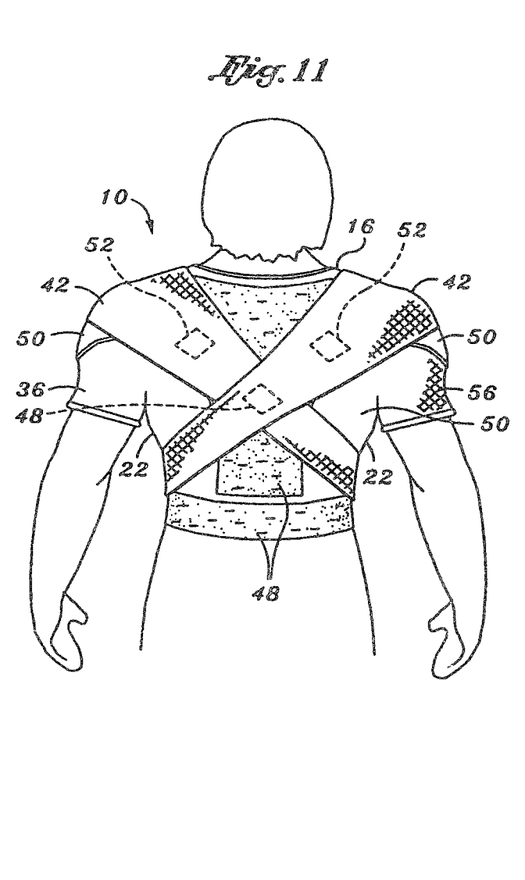
FIG. 11 is a back view of the posture improvement device of the alternative embodiment.
Figures 12, 13:
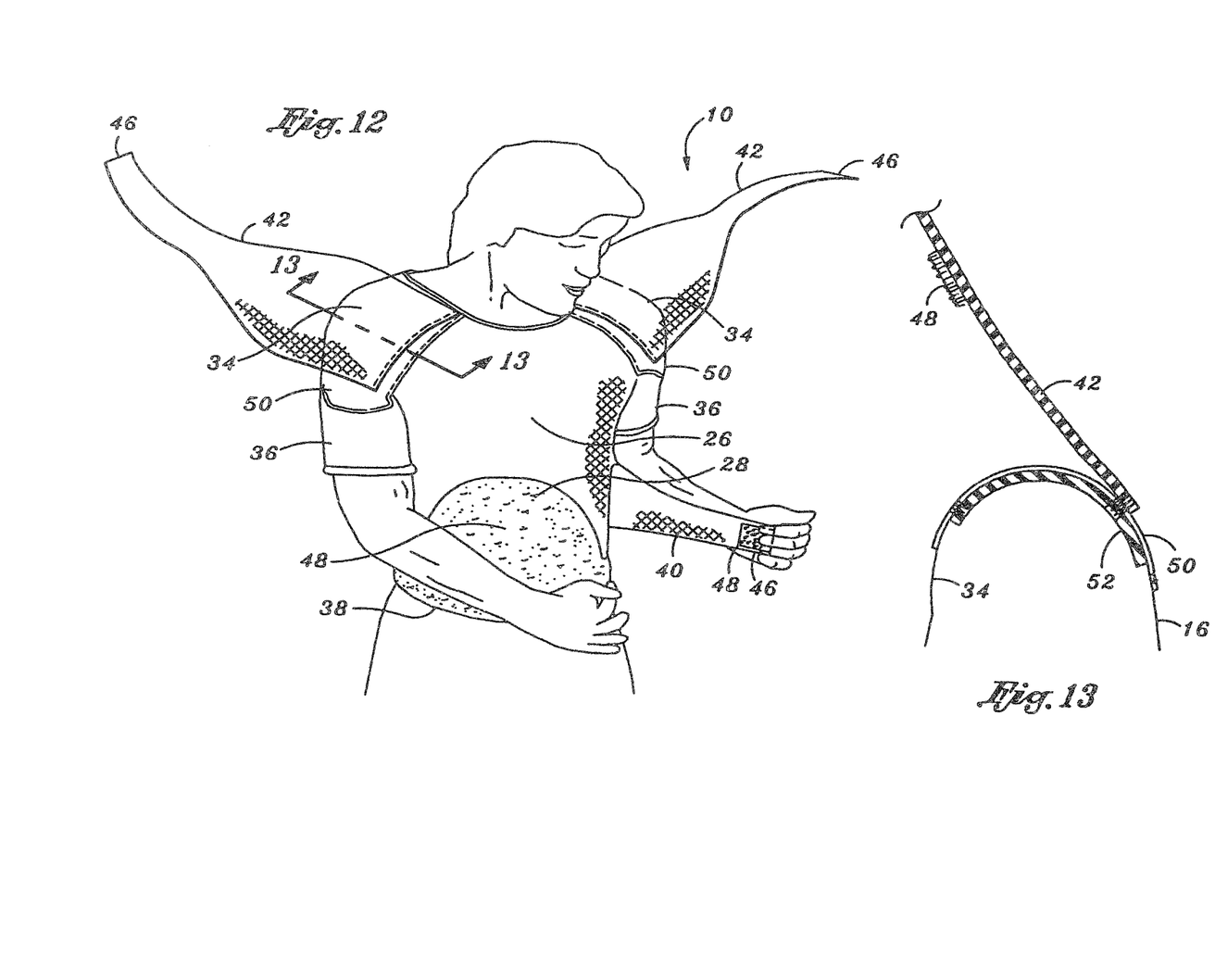
FIG. 12 is a perspective view of the posture improvement device of the alternative embodiment illustrating the patient adjusting the waist band.
FIG. 13 is a partial cross sectional view of the posture improvement device of the alternative embodiment taken along line 13-13 of FIG. 12 and illustrating the tension strap extending over a shoulder of the patient with the viscoelastic pad being disposed on the inner surface of the garment at the shoulder portion.
Figure 14:
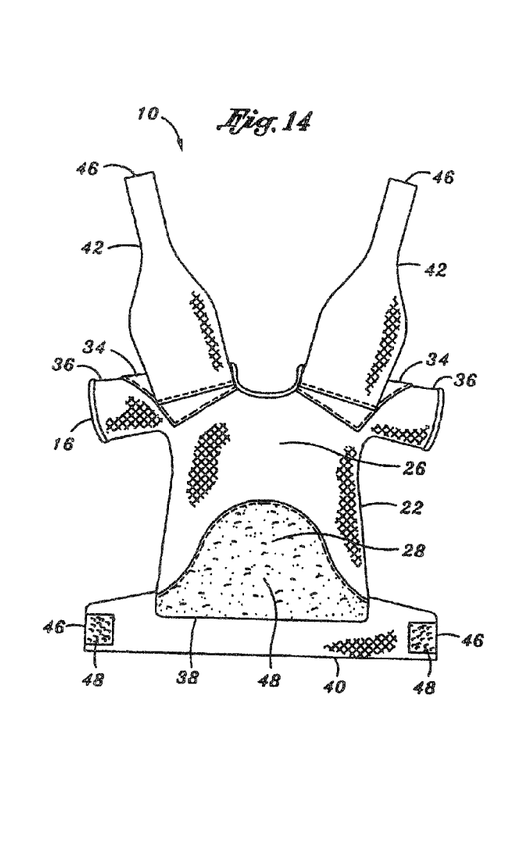
FIG. 14 is a view of a back side of the posture improvement device of the alternative embodiment and illustrating attachment points of the tension straps at the shoulder portions of the garment.

Advantageously, the tension straps 42 are configured to be stretchable or selectively adjustable relative to the garment 16 in a manner such that the patient's shoulders are generally biased downwardly while the patient's chest is generally biased outwardly. FIGS. 9-15 are views of the posture improvement device 10 in accordance with an alternative embodiment wherein the tension straps 42 are fixedly secured to the shoulder portions 34 of the garment 16. As best seen in FIGS. 9 and 12, the tension straps 42 of the device 10 of the alternative embodiment are configured to partially wrap laterally over partial sleeves 36 of the garment 16. The tension straps 42 of the alternative embodiment are positioned on the garment 16 in a manner similar to that of the preferred embodiment and are likewise configured to be stretchable or selectively adjustable such that the patient's shoulders are biased downwardly and the patient's chest is biased outwardly to promote proper posture.

Importantly, the device 10 is specifically adapted to provide neuromuscular stimulation using a combination of pressure, torque and angle simultaneously applied to the patient in order to train body muscles. When the device 10 is worn, proper posture of the patient may ultimately be achieved through muscle memory in a manner as will be described in greater detail below. Pressure may be applied to a surface of the patient's skin in order to stimulate cutaneous nerve receptors of the patient's skin. Such pressure is applied by the garment 16 which preferably is configured as a relatively tight, form-fitting shirt as described above. The garment 16 may be provided in a variety of sizes such as small, medium, and large to accommodate patients of differing sizes and shapes. Initial fitting of the device 10 may be provided by a health professional such as by a physical therapist or a chiropractor in a manner wherein the inner surface 18 of the garment 16 is generally and preferably tight fitting in order to allow for proper application of pressure to the patient's skin during wearing of the garment 16.

Referring more particularly now to FIGS. 1-8, shown is the device 10 as worn by the patient. As was earlier mentioned, the device 10 includes the garments 16 and the pair of extendable or stretchable tension straps 42. The garment 16 is configured to envelope at least a portion of the patient's torso 12 and at least a portion of the patient's upper arms 14. The garment 16 has an inner surface 18 and an outer surface 20, a front side 24, a back side 30, opposing lateral sides 22, and a pair of partial sleeves 36. As can be seen in FIGS. 1-8 as well as in FIGS. 9-15, the front side 24 includes a chest portion 26 and a stomach portion 28 while the back side 30 includes a back portion 32. In addition, the garment 16 defines opposing shoulder portions 34 and a waist portion 38 extending about a lower end of the garment 16.

Although shown in a preferred configuration of a short-sleeved undershirt, it is contemplated that the garment 16 may be provided in a variety of alternative configurations including, but not limited to, a sleeveless configuration. However, the short-sleeved configuration of the garment 16 is preferred in order to allow for effective training of the patient's pectoralis major muscles located on the patient's chest. In addition, the short-sleeved configuration of the garment 16 is preferred in order to enhance or improve the patient's range of motion, particularly the shoulder joints. Finally, the short-sleeved configuration of the garment 16 is preferred in order to allow for conditioning of the patient's rotator cuffs.

Regarding material from which the garment 16 may be fabricated, it is contemplated that stretchable yet taut material may be utilized in order to provide the desirable form-fitting feature such that pressure may be readily applied to the surface of the patient's skin in order to enhance neuromuscular stimulation thereto. In this regard, the garment 16 is preferably fabricated of elastomeric material, and is preferably sized and configured such that the inner surface 18 of the garment 16 is generally tightly disposed against the patient's skin when the garment 16 is worn. Such elastomeric material is also preferably breathable and/or which has moisture wicking capabilities in order to improve the patient's comfort level during periodic wearing of the device 10. Such material qualities may be provided by a combination of Lycra and Spandex although the garment 16 may be fabricated from a variety of alternative materials or combinations thereof Referring to FIGS. 1-15, the tension straps 42 are releaseably securable to the back portion 32 in diagonal relation to one another such that anatomical differences in patients may be accommodated. In addition, by orienting the tension straps 42 diagonally with respect to one another, pressure may be applied an angle in order to allow the device 10 to pull or bias each one of the patient's shoulders in a backwards or rearwards direction relative to the patient's spine. Such backward or rearward biasing allows for correction of forward slouching shoulders as may be characteristic of poor posture. As can be seen in FIGS. 1-8, each one of the tension straps 42 has opposed free ends 46 that are configured to be releaseably securable to the garment 16 at respective ones of the chest and stomach portion 26, 28. In the alternative embodiment of the device 10 shown in FIGS. 9-15, the tension straps 42 may be fixedly secured to the shoulder portions 34 such as be sewing in a manner best seen in FIGS. 13.

Figure 1:
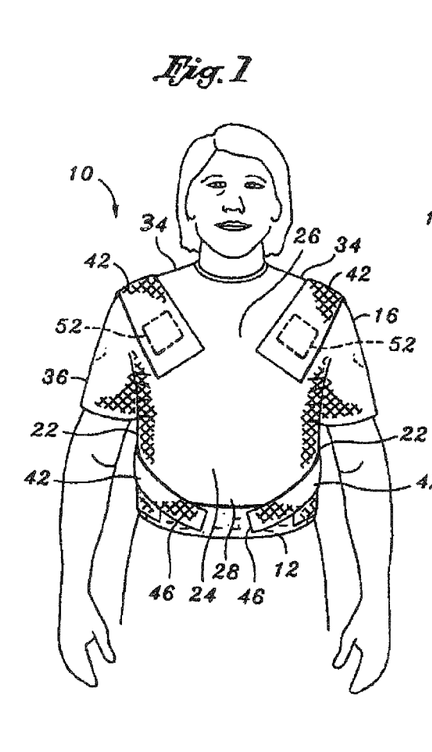
FIG. 1 is a front view of the posture improvement device of the present invention in accordance with a preferred embodiment comprising a garment having tension straps mounted thereon.
Figure 2:
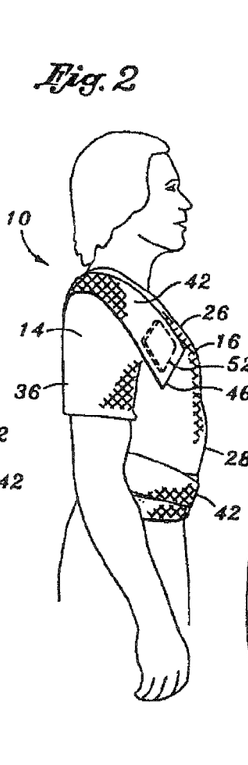
FIG. 2 is a side view of the posture improvement device of the preferred embodiment.
Figure 3:
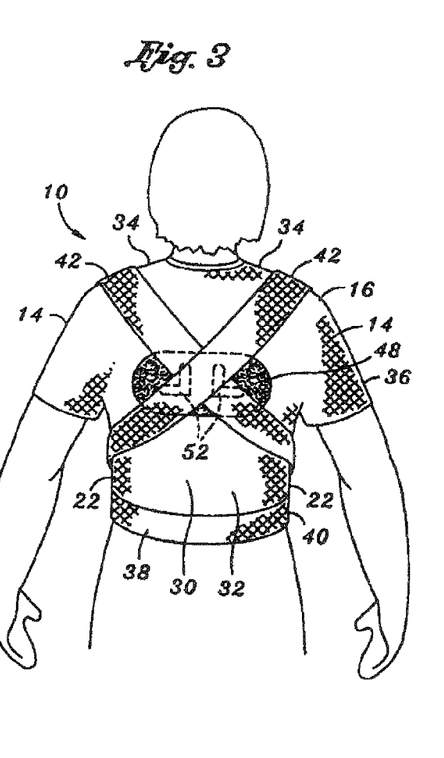
FIG. 3 is a back view of the posture improvement device of the preferred embodiment.

As shown in FIGS. 1-2 for the preferred embodiment of the device 10, an upper one of the free ends 46 of each one of the tension straps 42 is releaseably secured to the chest portion 26 on the outer surface 20 of the front side 24 of the garment 16. Referring to FIG. 3, the tension straps 42 are releaseably secured to the back portion 32 on the back side 30 of the garment 16 at an approximate center of the back portion 32. As can be seen, the tension straps 42 are diagonally disposed relative to one another at the back portion 32. Referring back to FIGS. 1-2, a lower end of each one of the tension straps 42 is releaseably secured to the waist portion 38 on the front side 24 of the garment 16. In this manner, each one of the tension straps 42 extends upwardly from the chest portion 26 adjacent one of the lateral sides 22, arches over one of the shoulder portions 34, passes diagonally across the back portion 32, partially wraps about the patient's torso 12 on the opposing one of the lateral sides 22, and terminates at the waist portion 38 on the front side 24.

Figure 10:
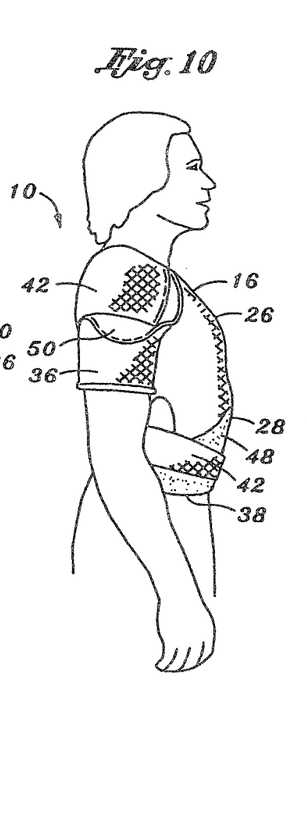
FIG. 10 is a side view of the posture improvement device of the alternative embodiment.

As shown in FIGS. 9-10 for the alternative embodiment, the upper one of the free ends 46 of each one of the tension straps 42 is fixedly secured to the chest portion 26 on the outer surface 20 of the front side 24 of the garment 16. However, as distinguished from the preferred embodiment, the tension straps 42 are configured to at least partially laterally wrap over adjacent ones of the partial sleeves 36 of the garment 16, as shown in FIG. 12. In this regard, the tension straps 42 of the alternative embodiment are wider at the shoulder portion 34 than for the tension straps 42 of the preferred embodiment. Referring to FIG. 11, the tensions traps 42 are releaseably secured to the back portion 32 on the back side 30 of the garment 16 at an approximate center of the back portion 32. As can be seen, the tension straps 42 are diagonally disposed relative to one another at the back portion 32. Referring back to FIGS. 9-10, the lower end of each one of the tension straps 42 is releaseably secured to the waist portion 38 on the front side 24 of the garment 16. The positioning and orientation of the tension straps 42 for the alternative embodiment is substantially similar to the positioning and orientation of the tension straps 42 for the alternative embodiment is substantially similar to the positioning and orientation of the tension straps 42 for the preferred embodiment.

Due to the angular orientation of the tension straps 42 in both of the embodiments, torque may be applied to the patient's torso 12 using a dual-anchor configuration of the straps wherein a first anchor is provided by extension of the tension straps 42 from the chest portion 26 on the front side 24 over the shoulder portion 34 and downwardly to the back portion 32 on the back side 30 of the garment 16. Because poor posture in a patient may typically be characterized by over-toned or shortened chest muscles due to a forward slouching position of the patient's chest, the first anchor of the tension straps 42 biases the shoulders rearwardly to open up the chest. A second anchor is provided by extension of the tension straps 42 from the back portion 32 on the back side 30 and partially wrapping about the patient's torso 12 to terminate at the waist portion 38 on the front side 24 of the garment 16.

Figures 4, 5, 6:
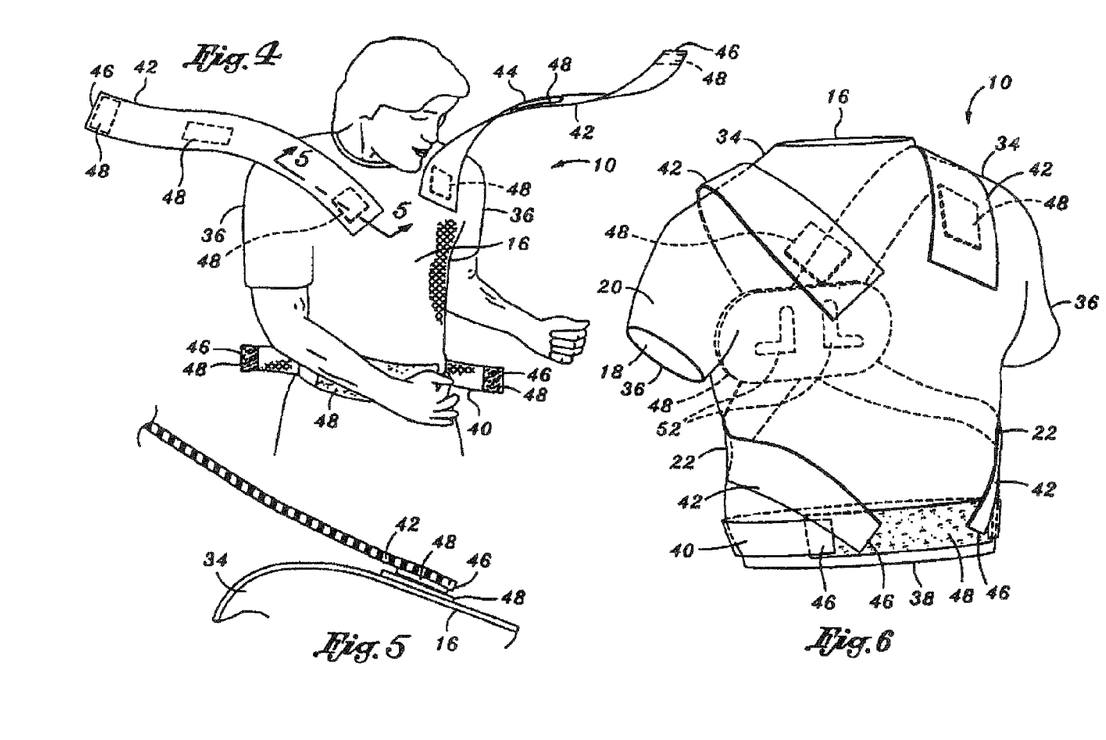
FIG. 4 is a perspective view of the posture improvement device illustrating a patient adjusting a waist band mounted on a waist portion of the garment.
FIG. 5 is a partial cross sectional view of the posture improvement device taken along line 5-5 of FIG. 4 and illustrating one of the tension strap releaseably secured to a chest portion and extending over a shoulder portion of the garment.
FIG. 6 is a perspective view of the posture improvement device of the preferred embodiment.

The device 10 of both the preferred and alternative embodiments may further comprise an elongate, extendable waist band 40 fixedly or releaseably secured to the waist portion 38 on the back side 30 of the garment 16. Similar to the tension straps 42, the waist band 40 has opposing free ends 46 that are configured to extend laterally outwardly from the back side 30 of the garment 16, as shown in FIGS. 4 and 12. Each one of the free ends 46 of the waist band 40 is configured to be wrapped partially around the patient's torso 12 and to be releaseably secured to the waist portion 38 on the front side 24 of the garment 16. The waist band 40 is preferably fabricated of elastomeric material such as Neoprene. However, a variety of material may be used to fabricate the waist band 40. For example, elastics typically used in underwear waistbands may be used to fabricate the waist band 40 of the device 10. The elastomeric material for use in the waist band 40 may be stretch yarn made of rubber.

Alternatively, the elastomeric material for use in the waist band 40 may be synthetic rubber material such as Spandex. Preferably, the material selected for use in the waist band 40 has appropriate stretch, recovery and spring characteristics such that tension may be continuously applied about the patient's waist in order to stabilize the lower ends of the tension straps 42 and prevent upward movement thereof. In addition, the elastomeric material is also preferably one that provides a soft surface and texture such that the waist band 40 is comfortable to wear against the tight-fitting garment 16. Likewise the tension straps 42 may also be fabricated of elastomeric material similar to material that may be used to fabricate the waist band 40 as described above. Although shown in FIGS. 1-8 as having a generally uniform width, each one of the tension straps 42 and the waist band 40 may be alternatively configured with a variable width, as is shown in FIGS. 9-15 of the alternative configuration of the device 10 and as was earlier described.

Referring the FIGS. 3, 8, 11 and 15, each one of the tension straps 42 may include a hook-loop panel 48 mounted adjacent a strap midpoint 44 such as by sewing or gluing. The hook-loop panel 48, more commonly referred to as Velcro, may be generally rectangularly shaped although various other shapes may be utilized. For example, the hook-loop panel 48 may generally span an entire length and width of each one of the tension straps 42. If the hook-loop panels 48 are provided as discrete elements, each one of the tension straps 42 may include the hook-loop panels 48 mounted in back-to-back arrangement to allow overlapping and anchoring of one of the tension straps 42 on top of the other one of the tension straps 42. In this regard, one of the tension straps 42 is sandwiched between the other one of the tension straps 42 and the garment 16 as is shown in FIGS. 3, 8, 11 and 15. By including hook-loop panels 48 in back-to-back arrangement on opposing faces of each one of the tension straps 42, either one of the tension straps 42 may be sandwiched without regard to relative positioning of the tension straps 42.

Figure 8:
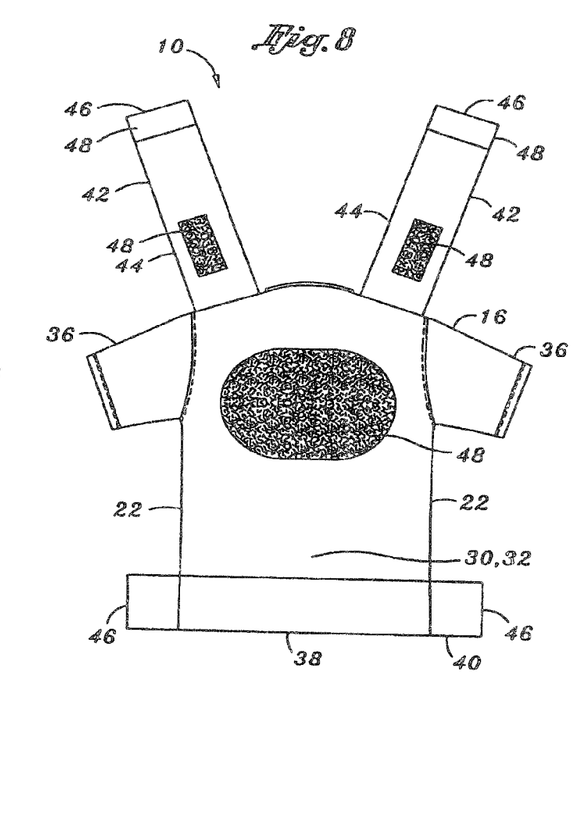
FIG. 8 is a view of a front side of the posture improvement device of the preferred embodiment and illustrating a hook-loop panel mounted on a back portion of the garment and viscoelastic pads mounted on an inner surface of the garment.
Figure 15:
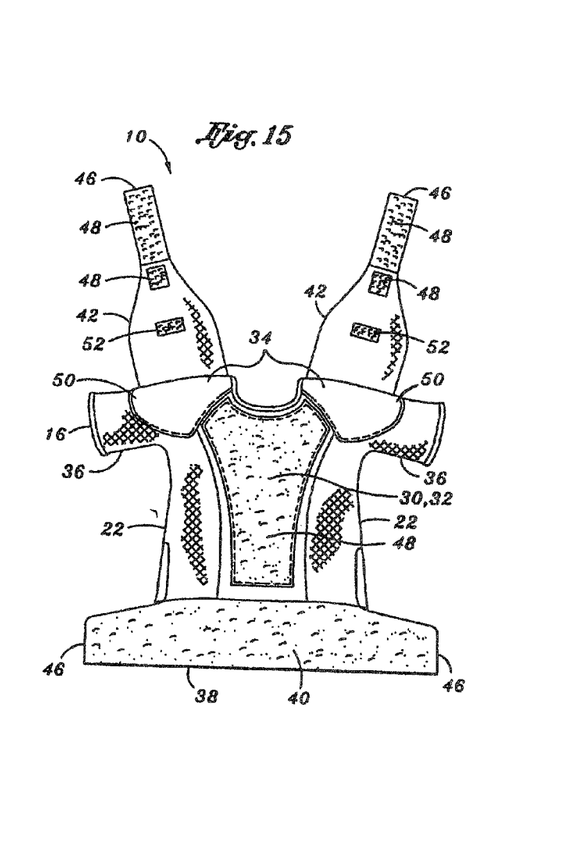
FIG. 15 is a view of a front side of the posture improvement device of the alternative embodiment and illustrating the hook-loop panel mounted on the back portion of the garment.

A mating hook-loop panel 48 may be mounted on the outer surface 20 of the back portion 32 such as by sewing, gluing or using any other suitable means. The hook-loop panel 48 of the back portion 32 may be provided in a generally larger size than the size of the hook-loop panel 48 mounted on the strap midpoints 44. For example, as shown in FIGS. 3 and 8 of the preferred embodiment, the hook-loop panel 48 of the back portion 32 may be configured to span a substantial portion of a width of the back portion 32. As shown in FIGS. 15 of the alternative embodiment, the hook-loop panel 48 of the back portion 32 may be configured as a generally elongate tapered panel extending from the waist portion 38 to the shoulder portions 34 of the back side 30 of the garment 16.

Providing the hook-loop panels 48 on the back portion 32 in the relatively larger size allows for greater flexibility in relative positioning of the tension straps 42 such that patients of varying anatomical shape and body development may be accommodated. In addition, the tension straps 42 may be releaseably secured thereto at the strap midpoints 44 which may allow for releaseably securement of the tensions traps 42 at any position on the back portion 32 of the garment 16. The generally large size of the hook-loop panel 48 of the back portion 32 allows for flexibility in initial positioning of the tension straps 42 as well as during progressive adjustment of tension in the tension straps 42 during the course of wearing the device 10.

Figure 7:
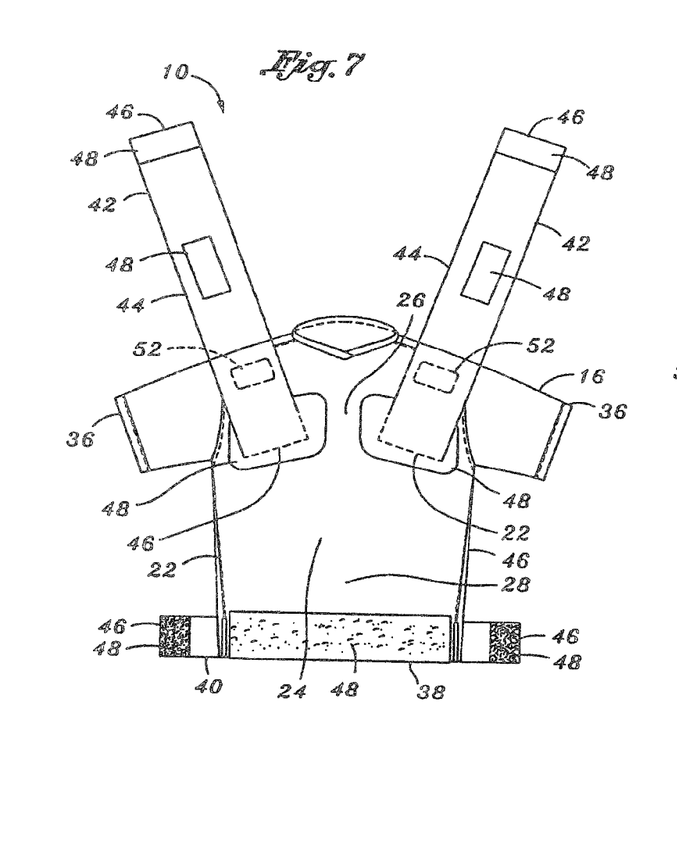
FIG. 7 is a view of a back side of the posture improvement device of the preferred embodiment and illustrating attachment points of the tension straps and the waist band.

In order to provide the capability of releaseably securing the tension straps 42 and waist band 40 as well as to allow for progressive adjustment of the tension therein, each one of the free ends 46 may include a hook-loop panel 48 mounted theron in a manner similar to that described above for the hook-loop panels 48 of the strap midpoints 44. Likewise, a mating hook-loop panel 48 may be mounted on the outer surface 20 of the garment 16 at respective ones of the chest portion 26 below the shoulder portions 34 and at the waist portions 38 on the front side 24. The hook-loop panel 48 may be configured to span a width of the front side 24 of the garment 16 as shown in FIGS. 7 and 15.

For the preferred embodiment of the device 10, the hook-loop panel 48 may be generally arch shaped as shown in FIGS. 9 and 12. In this manner, the free ends 46 of the tension straps 42 of the waistband may be releaseably secured to the garment 16 in order to provide the capability for adjustment of tension in the tension bands and in the waist band 40. As was earlier mentioned, the hook-loop panels 48 of the tension straps 42 may generally span an entire length and an entire width of each one of the tension straps 42 such that hook-loop material is generally integral with the tension straps 42.

For the preferred embodiment of the device 10, a spaced pair of the hook and loop panels 48 may be mounted on the outer surface 20 of the chest portion 26 for mating with the free ends 46 at upper ends of the tension straps 42, as shown in FIG. 5. Likewise, a hook and loop panel 48 may be mounted on the outer surface 20 of the waist portion 38 on the front side 24 of the garment 16 for mating with the free ends 46 at lower ends of the tension straps 42 as well as for mating with free ends 46 of the waist band 40. The hook and loop panels 48 of the chest portion 26 may be sized to be generally larger than that of the free ends 46 to allow for initial fitting and progressive adjustment of the tension straps 42. Similarly, the hook and loop panels 48 of the waist portion 38 may generally span across the front side 24 of the garment 16 at the waist portion 38 and may have a width that is generally larger than a width of either the tension bands or the waist band 40. Each one of the hook and loop panels 48 on the chest portion 26 and on the waist portion 38 may be mounted by sewing, gluing or other means in a manner similar to that described above.

Although not shown for the preferred embodiment in FIGS. 1-8 but as is shown for the alternative embodiment in FIGS. 9-15, reinforcement panels 50 may be included with the garment 16 on each one of the areas where the hook-loop panels 48 are mounted in the chest portion 26, as the back portion 32 and the waist portion 38. For example, in the alternative embodiment of the device 10 as shown in FIGS. 9-15, reinforcement panels 50 may be secured to the chest portion 26 below or surrounding the shoulder portions 34. Such reinforcement panels 50 may provide increased strength and resistance to pulling, stretching and tearing of the garment 16 against a continuous application of tension on the garment 16 through the tension straps 42 and through the waist band 40. The reinforcement panels 50 may be fabricated of material similar to or compatible with that used to fabricate the garment 16 and may be sewn, glued or attached to the garment 16 in any suitable manner.

Referring more particularly now to FIGS. 6 and 7 for the preferred embodiment of the device 10, shown are a spaced apart pair of viscoelastic pads 52 releaseably mounted on the inner surface 18 at the chest portion 26 above or adjacent to the free ends 46 mounted on the outer surface 20 of the garment 16. In this regard, the viscoelastic pads 52 are preferably positioned on or adjacent to the patient's pectoralis major muscles located on the patient's chest. The viscoelastic pads 52 are configured to substantially contact the patient's skin in order to restrict movement of the free ends 45 relative to the patient's skin.

In this manner, the viscoelastic pads 52 may stop slippage of the garment 16 such that the tension straps 42 may better bias the patient's shoulder rearwardly allowing the device 10 to push the patient's chest out. In addition, neuromuscular stimulation may be provided by the viscoelastic pads 52 to the patient's skin to enhance posture correction. The viscoelastic pads 52 may be provided in any shape although the generally rectangular shape shown in FIGS. 6 and 7 is believed to be advantageous. The viscoelastic pads 52 may be secured to the inner surface 18 of the garment 16 using hook-loop panels 48 in a manner similar to that described above for the free ends 46 of the tension straps 42. In this manner, the relative position of the viscoelastic pads 52 may be adjusted to accommodate the character of the patient's anatomy and development.

Likewise for the alternative embodiment of the device 10 illustrated in FIG. 13, the pair of viscoelastic pads 52 may be mounted on the inner surface 18 at the shoulder portions 34. Similar to the configuration of the viscoelastic pads 52 on the chest portion 26 of the preferred embodiment, the viscoelastic pads 52 on the shoulder portions 34 of the alternative embodiment are configured to substantially contract the patient's skin in order to restrict movement of the tension straps 42 so as to better bias the patient's shoulder rearwardly.

Referring now to FIGS. 3 and 8, shown is the device 10 having a spaced apart pair of laterally outwardly facing L-shaped viscoelastic pads 52 releaseably mountable on the inner surface 18 of the garment 16. As shown, the viscoelastic pads 52 are positioned at the back portion 32 of the garment 16 below each one of the shoulder portions 34. Although other shapes such as squares and rectangles may be used, the L-shaped configuration of the viscoelastic pads 52 is believed to be advantageous in that such a shape may be partially engageable with the patient's scapula which is generally located towards back of the patient's rib cage.

Engagement of the L-shaped viscoelastic pads 52 with the patient's skin may limit dynamic movement of the tension straps 42 during body movements of the patient while wearing the device 10. In this regard, the L-shaped viscoelastic pads 52 may engage a lower corner of the patient's scapula to help stabilize and enhance the development of proper posture. The viscoelastic pads 52 may also be mounted on the inner surface 18 of the back portion 32 of the garment 16 as shown in FIG. 11. Although shown as being generally rectangularly shaped in FIG. 11, the viscoelastic pads 52 may be generally L-shaped as provided in the preferred embodiment. The L-shaped viscoelastic pads 52 may preferably be provided in three different sizes corresponding to small, medium and large sizes of the garment 16. In this manner, the viscoelastic pads 52 may be compatible with the varying anatomies of patients wearing the device 10.

Although not shown, further stabilization of the lower ends of the tension straps 42 may be provided by a spaced pair of viscoelastic pads 52 releaseably mounted on the inner surface 18 of the garment 16 opposite the free end 46 termination areas at the waist portion 38 on the front side 24 of the garment 16. Such viscoelastic pads 52 may be generally formed as an elongate shape or in a rectangular shape and may be secured to the inner surface 18 using hook-loop panels 48 in a manner similar to that described above. Such viscoelastic pads 52 may provide stabilization for lower ends of each one of the tension straps 42 against dynamic movement to enhance development of proper posture.

Preferably, each one of the viscoelastic pads 52 are fabricated from flexible, rubber like material such as silicone rubber material although any resilient material may be used to provide a soft and semi-tacky surface to comfortably bear against the patient's skin and which will prevent relative slippage or movement of the tension straps 42. Toward this end, each one of the viscoelastic pads 52 may include a texture or pattern in a surface thereof in order to provide improved gripping of the patient's skin. Such pattern may additionally improve neuromuscular stimulation of nerve receptors in the patient's skin and may provide focused compression thereagainst.

It is recognized that there are an infinite variety of materials from which the viscoelastic pads 52 may be fabricated. In order to enhance neuromuscular stimulation, it is contemplated that the each one of the viscoelastic pads 52 may include a heating element configured to provide heat therapy to the patient's torso 12 by elevating the temperature of the viscoelastic pads 52. Furthermore, each one of the viscoelastic pads 52 may include an electrostimulation element configured to provide and enhance neuromuscular stimulation to the patient's torso 12.

The operation or method of using the device 10 of the present invention will now be described for both the preferred and alternative embodiments with particular reference to FIGS. 4 and 12. In the method for improving the body alignment of the patient's upper torso 12, the posture improvement device 10 as described above is utilized wherein the device 10 comprises the garment 16 and at least the tension straps 42. As was earlier mentioned, the garment 16 is configured to envelope the patient's torso 12 and at least a portion of the patient's upper arms 14. The garment 16 has the inner surface 18 and the outer surface 20, a front side 24, and back side 30, opposing ones of lateral sides 22 and the pair of partial sleeves 36. The front side 24 includes the chest portion 26 and a stomach portion 28. The back side 30 includes the back portion 32. The garment 16 defines the opposing shoulder portions 34 and the waist portion 38 which extends about the garment 16 at a lower end thereof. The device 10 further comprises the pair of tension straps 42 releaseably secured to the back portion 32 in diagonal relation to one another as was earlier described.

The method of using the device 10 comprises the steps of initially putting on or applying the garment 16 to the patient such that the garment 16 envelopes the patient's torso 12 with the patient's arms extending through the partial sleeves 36 and the patient's head and neck extending through a neck hole of the garment 16. Initial fitting of the garment 16 is preferably performed by a health professional such that a tight fit is provided by the garment 16 against the patient's skin. Once the garment 16 is placed on the patient, the tension straps 42 may then be attached to the back portion 32 in diagonal relation to one another at respective ones of the strap midpoint 44, as is shown in FIGS. 3 and 11.

For the preferred embodiment, the tension straps 42 are applied with the free ends 46 of each one of the tension straps 42 being extended diagonally upwardly from the back portion 32 and over one of the shoulder portions 34 to releaseably secure the free end 46 to the chest portion 26 on the front side 24. For the alternative embodiment of the device 10 wherein the upper end of the tension straps 42 may be fixedly secured to the shoulder portions 34, the tension straps 42 are applied in reverse order to that described above with the tension straps 42 being extended over the shoulder portions 34 and stretched diagonally downwardly and releaseably secured to the back portion 32.

Following securement of the tension straps 42 to the back portion 32, the remaining ones of the free ends 46 of each one of the tension straps 42 are extended diagonally downwardly across a lower part of the back portion 32 and partially wrapped about the patient's torso 12 on the opposing one of the lateral sides 22. The free ends 46 are then releaseably secured to the waist portion 38 on the front side 24 as shown in FIGS. 1 and 9. Following their initial application, the tension in the tension straps 42 may be adjusted by positioning or moving the free ends 46 relative to the garment 16 such that the patient's shoulders are biased generally downwardly and the patient's chest is biased generally outwardly and the patient's back is generally straightened out from a hunched over position. Finally, the free ends 46 of the waist band 40 are extended laterally about the patient's torso 12 where the free ends 46 are secured to the waist portion 38 on the front side 24.

If viscoelastic pads 52 are included with the device 10 of the preferred embodiment, the viscoelastic pads 52 are positioned in spaced relation on the inner surface 18 at the chest portion 26 above the free ends 46 mounted adjacent thereto on the outer surface 20. If viscoelastic pads 52 are included with the device 10 of the alternative embodiment, the viscoelastic pads 52 are positioned in spaced relation on the inner surface 18 of the shoulder portions 34 of the garment 16. The pair of L-shaped viscoelastic pads 52 may also be positioned on the inner surface 18 at the back portion 32 below each one of the shoulder portions 34.

The L-shaped viscoelastic pads 52 may be positioned on the hook-loop panels 48 such that the L-shaped viscoelastic pads 52 are partially engagable with the patient's scapula which is generally located on the patient's back adjacent the patient's rib cage. However, it is recognized that the viscoelastic pads 52 may be provided in any location on the patient's in a manner that will provide stability or anchoring of the tension straps 42. Finally, a pair of the viscoelastic pads 52 maybe provided on the inner surface 18 opposite the free end 46 termination areas at the waist portion 38 on the front side 24 to add stability of the tension straps 42. Following installation and initial positioning of the viscoelastic pads 52, final adjustments thereof may be made relative to the garment 16 such that movement of the free ends 46 relative to the patient's skin is generally restricted.

To summarize, the present invention uniquely functions, due to its proprioceptive approach, to address the following conditions:

a) upper trapezium pain,
b) rotator cuff weakness, by optimizing scapular position to improve the rotator cuff muscle,
c) mid-thoracic pain, by decreasing tension in the periscapular muscles,
d) scapular dyskinesis,
e) biceps tendinitis,
f) thoracic outlet syndrome,
g) impingement syndrome, and
h) glenohumeral instability.

Additional modifications and improvements of the present invention may also be apparent to those of ordinary skill in the art. Thus, the particular combination of parts described and illustrated herein is intended to represent only certain embodiments of the present invention, and is not intended to serve as limitations of alternative device 10s within the spirit and scope of the invention.

What is claimed is:

1. A device for improving the posture of a patient, the device comprising:
   a garment having a torso portion configured to envelop at least a portion of the patient's torso and at least a portion of the patient's upper arms, the garment having an inner and outer surface, a front side, a back side, opposing lateral sides, and a pair of partial sleeves, the front side including a chest portion and a stomach portion, the back side including a back portion on the torso portion, the garment defining opposing shoulder portions and a waist portion extending about the garment;
   a pair of extendable tension straps each having a first fastener adjacent to a strap midpoint, the first fasteners of the pair of extendable tension straps being releasably securable to the back portion in diagonal relation to one another, each one of the tension straps having opposed free ends configured to be releasably securable to the garment at respective ones of the chest and stomach portion, each one of the tension straps originating at and extending upwardly from the chest portion adjacent to one of the lateral sides, arching over one of the shoulder portions, passing diagonally across the back portion, partially wrapping about the patent's torso portion on the opposing one of the lateral sides, and terminating at the waist portion on the front side; and
   a portion of the back portion of the garment having a second fastener configured for affixing the first fasteners of the pair of extendable straps on the back portion of the garment.

2. The device of claim 1 further comprising a waist band fixedly secured to the waist portion on the back side and having opposing free ends extending laterally outwardly therefrom and configured to be wrapped partially around the patient's torso and releaseably secured to the waist portion on the front side.

3. The device of claim 2, wherein the first fastener of each one of the tension straps includes a hook-loop panel mounted adjacent a strap midpoint; and
   wherein the second fastener includes an additional planar fabric layer comprises a mating hook-loop panel being mounted on the outer surface of the back portion such that the tension straps may be releaseably secured thereto at the strap midpoints.

4. The device of claim 3, wherein each one of the free ends includes a hook-loop panel mounted thereon; and further comprising:
   a mating hook-loop panel being mounted on the outer surface at respective ones of the chest portion below the shoulder portions and at the waist portion of the front side such that the free ends may be releaseably secured thereto for allowing adjustment of an amount of tension in the tension bands and waist band.

5. The device of claim 1, wherein the tension straps are secured to an approximate center of the back portion on the second fastener.

6. The device as claimed in claim 1, wherein the garment includes a pair of reinforcement panels secured to the chest portion below the shoulder portions.

7. The device of claim 1 wherein the tension straps are fabricated from elastomeric material.

8. The device of claim 1 wherein the garment is fabricated of elastomeric material and being sized and configured such that the inner surface is generally tightly disposed against the patient's skin when the garment is worn.

9. The device of claim 8 wherein the elastomeric material is comprised of a combination of Lycra and Spandex.

10. The device of claim 1 further comprising:
    a spaced apart pair of visoelastic pads releasably mounted on the inner surface at the chest portion above the free ends mounted adjacent thereto on the outer surface;
    wherein the viscoelastic pads are configured to substantially contact the patient's skin in order to restrict movement of the free ends relative to the patient's skin.

11. The device of claim 10, further comprising:
    a spaced apart pair of shaped viscoelastic pads releasably mountable on the inner surface at the back portion below each one of the shoulder portions, the pair of shaped viscoelastic pads being disposed below the second fastener.

12. The device of claim 11 further comprising:
    a spaced apart pair of viscoleastic pads releaseably mounted on the inner surface opposite the free and termination areas at the waist portion on the front side.

13. The device of claim 10 wherein the viscoelastic pads are fabricated of silicone rubber material.

14. The device of claim 10 wherein each one of the viscoelastic pads includes a heating element configured to provide heat to the patient's torso.

15. The device of claim 10 wherein each one of the viscoelastic pads includes an electrostimulation element configured to provide neuromuscular stimulation to the patient's torso.

* * * * *